United States Patent [19]
Ono et al.

[11] Patent Number: 5,534,523
[45] Date of Patent: Jul. 9, 1996

[54] ANTI-AIDS VIRUS COMPOSITION

[75] Inventors: Minoru Ono, Tokyo, Japan; Yuka Tamura, St. Petersburg, Fla.; Michinori Akasu, Tokyo, Japan

[73] Assignee: Kaken Shoyaku Co., Ltd., Tokyo, Japan

[21] Appl. No.: 353,376

[22] Filed: Dec. 2, 1994

Related U.S. Application Data

[63] Continuation of Ser. No. 38,060, Mar. 29, 1993, abandoned, which is a continuation of Ser. No. 751,844, Aug. 29, 1991, abandoned.

[30] Foreign Application Priority Data

Aug. 29, 1990 [JP] Japan .................................. 2-225253

[51] Int. Cl.$^6$ .................................................. A61K 31/435
[52] U.S. Cl. ........................................... 514/308; 514/279
[58] Field of Search ..................................... 514/308, 279

[56] References Cited

FOREIGN PATENT DOCUMENTS

| | | |
|---|---|---|
| 8907384 | 8/1989 | WIPO . |
| 9005523 | 5/1990 | WIPO . |

OTHER PUBLICATIONS

Japanese Pharmacology & Therapeutics, vol. 17, No. 11, Nov. 1989, pp. 239–243, JP; K. Shimura: "Effect of cepharanthin on complement C3 and peritoneal macrophages in mice" (Abstract)(only).

Immunobiology, vol. 170, No. 4, Nov. 1985, pp. 351–364; Y. Nihashi et al.: "Thymus–dependent increase in number of T cells in parathymic lymph nodes . . ." Abstract only, p. 352; pp. 361–363.

Japanese Journal of Cancer and Chemotherapy, vol. 15, No. 1, 1988, pp. 127–133, JP; M. Ono et al.: "Augmentation of murine organ–associated natural immune responses by cepharanthin" Abstract (only).

"The Merck Manual," 15th edition, 1987, pp. 288–294, Merck & Co., Inc., Rahway, N.J.

Planta Medica, vol. 56, Dec. 1990, pp. 654–655; International Symposium, "Biology and Chemistry of Active Natural Substances," Bonn, 17th–22nd, Jul. 1990; K. Fujitani et al.: Inhibitory effect . . . .

Journal of the Medical Society of Toho University, vol. 34, No. 3.4, Nov. 1987, pp. 280–285; Shirai et al.: "Interferon inducing activity of cepharanthin and the effect of cepharanthin . . .".

Sei Marianna Ika Daigaku Zasshi, vol. 9, No. 3, 1981, pp. 253–265; T. Kuramori et al.: "Effect of cepharanthin on cellular immunity" Abstract only.

Nippon Igaku Hoshasen Gakkai Zasshi, vol. 37, No. 12, 1977, pp. 1153–1167; R. Makidono et al.: "Leukopenia and lymphopenia during the radiation therapy and their recovery by . . ." Abstract only.

Journal of Ethnopharmacology, vol. 20, pp. 107–120, 1987.

Merck Index 11, p. 306, 1981 Cepharanthine, 1989.

Science, vol. 249, pp. 1533–1543, Sep. 1990.

Biochemical Pharmacology, vol. 39, No. 7, pp. 1255–1259, 1990.

Cancer Research, vol. 48, pp. 1307–1311, Mar. 1, 1988.

*Primary Examiner*—Jerome D. Goldberg

[57] ABSTRACT

An anti-AIDS virus composition comprising a therapeutically effective amount of cepharanthine or a pharmaceutically acceptable salt thereof and a method for treating AIDS which comprises administering a therapeutically effective amount of cepharanthine or a pharmaceutically acceptable salt thereof are disclosed.

4 Claims, No Drawings

ANTI-AIDS VIRUS COMPOSITION

This is a continuation of application No. 08/038,060 filed Mar. 29, 1993, now abandoned, which is a continuation of application No. 07/751,844 filed Aug. 29, 1991, now abandoned.

FIELD OF THE INVENTION

The present invention relates to an anti-AIDS virus composition containing cepharanthine as an effective ingredient. Furthermore, the present invention relates to a method for treating AIDS, a method for preventing the onset of AIDS, and a method for inhibiting proliferation of AIDS virus.

BACKGROUND OF THE INVENTION

Acquired immunodeficiency syndrome (AIDS) is a serious immunodeficiency disease caused by infection with AIDS virus, i.e., human immunodeficiency virus (HIV). Because of its extremely high risk of death, there is a pressing social need for countermeasures, but no effective therapeutic modality or vaccine has been developed as yet. The only known anti-AIDS virus agent that has been approved by the Food and Drug Administration of the United States is azidothymidine (AZT). However, this drug has not only high toxicity but has the drawback that repeated administration over one year results in development of resistance to AZT in AIDS virus. Therefore, the advent of a more useful therapeutic agent has been keenly demanded (Science 249, 1533–1543 (1990)).

The present inventors have conducted the extensive investigations to solve the above problems and found that cepharanthine is useful as an active ingredient in an anti-AIDS virus composition. The present invention has been accomplished based on such findings.

SUMMARY OF THE INVENTION

Thus, the present invention provides an anti-AIDS virus composition comprising a therapeutically effective amount of cepharanthine or a pharmaceutically acceptable salt thereof. Furthermore, the present invention provides a method for treating AIDS, a method for preventing the onset of AIDS, and a method for inhibiting proliferation of AIDS virus, each of which comprises administering a therapeutically effective amount of cepharanthine or a pharmaceutically acceptable salt thereof.

DETAILED DESCRIPTION OF THE INVENTION

Cepharanthine is a plant alkaloid represented by the following formula (I) (Merck Index 11, 306, 1981 Cepharanthine (1989); U.S. Pat. Nos. 2,206,407 and 2,248,241; and Japanese Patents 120,483, 128,533, and 141,292).

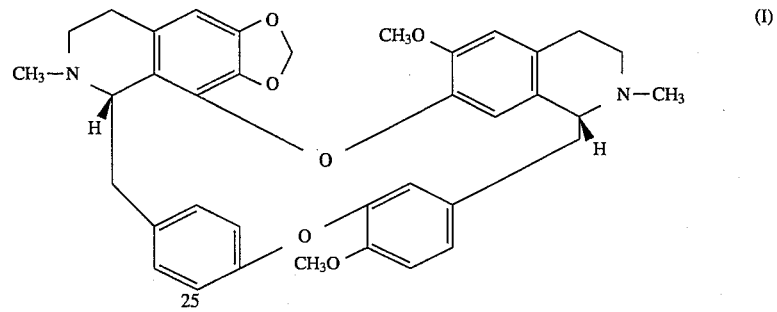

Cepharanthine has antiallergic, immunomodulating, antiplatelet aggregation, anticancer drug resistance inhibitory and other activities (Journal of Ethonopharmacology 20, 107–120 (1987); Cancer Research 48, 1307–1311 (1988); and Biochemical Pharmacology 39, 1255–1259 (1990)), and has been clinically employed broadly as a safe drug with a minimum of side effect in the treatment of leukocytopenia, alopecia areata, exudative otitis media, viper bites, etc. However, it has not been known that cepharanthine has an anti-AIDS virus activity.

Cepharanthine, which is used in the present invention, can be extracted from such plants as *Stephania cepharantha*, *Stephania sasakii*, etc. of the family *Menispermaceae*. Any of a vacuum-concentrated cepharanthine extract, the precipitate formed on alkalinization of an acid solution of the extract, the alkaloid fraction separated therefrom, and the crop of crystals available by the conventional isolation and purification can be employed for the purposes of the present invention. Pharmaceutically acceptable salts of cepharanthine can be also employed for the purposes of the present invention. Such salts include addition salts with acids such as hydrochloric acid and sulfuric acid, etc.

These various cepharanthine-containing compositions can be prepared by the conventional methods (cf. U.S. Pat. Nos. 2,206,407 and 2,248,241; Japanese Patents 120,483, 128,533, and 141,292; and Yakugaku Zassi 89, 1678–1681 (1969), etc). For example, cepharanthine may be extracted with an organic solvent such as methanol, ethanol, acetone, ether, and benzene or with an aqueous solution of acid such as hydrochloric acid, sulfuric acid, acetic acid, and citric acid. The cepharanthine-containing solution extracted with the organic solvent may be concentrated under atmospheric pressure or reduced pressure. The acid solution of thus concentrated cepharanthine extract or the above-mentioned acid extract may be alkalinized with sodium hydroxide or ammonia, etc., and then extracted with an organic solvent which does not mix with water such as ether, benzene, hexane, and chloroform to give the alkaloid fraction.

The anti-AIDS virus composition may be cepharanthine or a pharmaceutically acceptable salt thereof as such or an extract containing cepharanthine or alkaloid fraction containing cepharanthine, but is usually provided as formulated with a generally usable amount of usual excipient, binder, lubricant, solvent and/or stabilizer, in such dosage forms as tablets, powder, granules, capsules and injections, etc.

The excipient mentioned above includes, among others, starch, lactose, methylcellulose, crystalline cellulose, synthetic aluminum silicate and so on. The binder includes, among others, hydroxypropylcellulose and polyvinylpyrrolidone. The lubricant includes, among others, talc, magnesium stearate, calcium stearate and so on.

The dosage of the anti-AIDS virus composition of the present invention varies based on the patient's age, body weight and condition, etc. Generally speaking, however, the dosage is about from 10 to 1,000 mg/day, preferably about from 30 to 300 mg/day, as the active ingredient, in the case of oral administration, and about form 10 to 300 mg/day, preferably about from 50 to 200 mg/day, as the active ingredient, in the case of intravenous administration. Such dose is administered in a single dose or in two or three divided doses in the case of oral administration, and generally administered in a single dose in the case of intravenous administration.

Cepharanthine has an inhibitory effect on the production of AIDS virus. That is, cepharanthine is capable of inhibiting the proliferation of AIDS virus. Thus, cepharanthine is useful as an anti-AIDS virus composition for treating AIDS or for preventing the onset of AIDS.

The following examples are further illustrative of the present invention, but not by way of limitation.

PREPARATION EXAMPLE 1

Cepharanthine hydrochloride (500 mg), lactose (3.0 g), corn starch (1.28 g), hydroxypropylcellulose (200 mg) and magnesium stearate (20 mg) are mixed well, granulated and compression-molded into a tablet containing 100 mg of the active ingredient.

PREPARATION EXAMPLE 2

The alkaloid fraction of *Stephania sasakii* (500 mg), lactose (2.5 g), potato starch (1.75 g), crystalline cellulose (240 mg) and calcium stearate (10 mg) are mixed well and the mixture is filled into a gelatin capsule to give a capsule containing 10 mg of the active ingredient.

PREPARATION EXAMPLE 3

The alkaloid fraction of Stephania cepharantha (500 mg) is dissolved in dilute hydrochloric acid, made up with distilled water for injection and isotonized with sodium chloride to make a total of 100 ml. This solution is filtered through a 0.2 μ membrane filter and distributed into 10 ml ampules, which are then sealed and heat-sterilized to give an injection.

The first sign that cepharanthine has impact on AIDS virus infection was provided by experiments wherein CEM-CDC cells infected with a high multiplicity of HIV-1 were protected from cytolysis. That is, CEM-CDC cells ($5\times10^5$ cells/ml) died in culture 3 days after infection with HIV-1 ($10^8$ TCID$_{50}$/ml; TCID: tissue culture mean infectious dose), but survived the infection if the cultures were maintained in medium containing cepharanthine. The anti-AIDS virus effects of cepharanthine were confirmed in HIV-1-infected CEM-CDC cells as follows.

TEST EXAMPLE

The N1T strain of HIV-1 which was isolated from a patient with AIDS in New York[1] was used as the virus. The CD4-positive human T-cell line, CEM[2], that was obtained from the Centers for Disease Control, called CEM-CDC cell was used as the host cell. The virus was propagated in CEM-CDC cells and filtered with 0.8-μm Nalgen filters (Millipore) before use.

[1] Casareale, Do, et al., AIDS Res. 1, 407–421 (1985) [2] Foley, G. E., et al., Cancer 18, 522–529 (1965)

Target cells (CEM-CDC; $1\times10^6$ cells) were incubated with HIV-1 ($2\times10^5$ TCID$_{50}$) under 5% of $CO_2$ for 3–4 hours at 37° C. The infected cells were washed extensively (3–5 times) and maintained in medium [RPMI-1640 tissue culture medium supplemented with 5% (vol/vol) heat-inactivated fetal calf serum, 100 U/ml penicillin G, and 100 μg/ml streptomycin] containing various concentration of a cepharanthine. As the control, CEM-CDC cells were maintained in medium alone. In all experiments, the infected cells ($2\times10^5$ cells per 1.5 ml) were distributed into a 24-well culture plate and incubated under 5% of $CO_2$ at 37° C. for 5 days. After incubation, the culture supernatants containing HIV-1 major gag or core protein, p24, were collected and filtered through 0.45-μm filters. The concentration of HIV-1 p24 antigen in filtered cell-free supernatant was measured with an enzyme immunoassay specific for HIV-1 (Abbot Laboratory, N. Chicago, Ill., U.S.A.)[3] approved by the U.S. Food and Drug Administration for research use. Briefly, varying dilution of test supernatants were allowed to incubate with anti-p24 antibody-coated beads. Dilutions of known p24 standards (0–1,000 U p24/ml) mixed with the beads acted as controls. After extensive washing, the beads were allowed to react with a p24-specific rabbit antibody. After washing, the beads were reacted with a horseradish peroxidase-conjugated goat anti-rabbit IgG, developed with o-phenylenediamine and the absorbance value was read at 492 nm. Concentration of p24 (U/ml) was read from the standard curve derived from dilutions of the known standard by a commercially available p24 capture assay (Coulter™ HIV Antigen Assay kit; Coulter Corporation, Hialeah, Fla., U.S.A.)[4,5] using an ELISA test.

[3] Goudsmit, J., et al., Lancet II: 177–180 (1986) [4] Casey, J. M., et al., J. Virology 55, 417–423 (1985) [5] Veronese, F. D., et al., Proc. Natl. Acad. Sci. USA 82, 5199–5202 (1985)

The percent inhibition of HIV-1 replication is given by $[1-(T/C)]\times100$, where T is the amount of p24 antigen in supernatant of culture treated with drugs, and C is the amount of p24 antigen in supernatant of culture treated without drugs. The results are shown in Table 1.

Viability of cells in culture was determined by trypan blue exclusion counting and calculated as: Percent cell viability= $(V/T)\times100$, where V=number of viable cells and T=total cell count. The results are shown in Table 2.

TABLE 1

| Concentration of Cepharanthine (μg/ml) | HIV-1 p24 antigen (pg/ml) | Percent inhibition |
| --- | --- | --- |
| 0 | 256,400 | 0 |
| 3 | 188,767 | 26.4 |
| 10 | 97,677 | 61.9 |
| 30 | 10,830 | 95.8 |

TABLE 2

| Concentration of Cepharanthine (µg/ml) | Percent cell viability in culture Days 5 |
| --- | --- |
| 0 | 96.3 |
| 3 | 97.5 |
| 10 | 93.3 |
| 30 | 85.8 |

As shown in Table 1, supernatants of CEM-CDC cell cultures maintained in medium containing cepharanthine after infection with HIV-1 contained a lower concentration of p24 antigen when compared with infected CEM-CDC cell cultures maintained in medium alone. From these results, it is apparent that cepharanthine inhibited HIV-1 production. The percent inhibition of HIV-1 production increased with the concentration of cepharanthine used to treat the cultures. Moreover, cepharanthine at the concentrations utilized didn't have any toxic effect on CEM-CDC cells as shown in Table 2.

While the invention has been described in detail and with reference to specific embodiments thereof, it will be apparent to one skilled in the art that the various changes and modifications can be made therein without departing from the spirit and scope thereof.

What is claimed is:

1. A method of treating AIDS which comprises administering cepharanthine or a pharmaceutically acceptable salt thereof to a patient infected with AIDS Virus in a therapeutically effective amount for treating AIDS.

2. A method for preventing an onset of AIDS which comprises administering cepharanthine or a pharmaceutically acceptable salt thereof to a human carrier of AIDS virus in a therapeutically effective amount for preventing an onset of AIDS.

3. A method for inhibiting proliferation of an AIDS virus in a human body which comprises administering to said body cepharanthine or a pharmaceutically acceptable salt thereof in a therapeutically effective amount for inhibiting proliferation of an AIDS virus.

4. A method of treating human lymphocyte cells infected with the AIDS virus comprising administering cepharanthine or a pharmaceutically acceptable salt thereof to a human lymphocyte cells infected with AIDS in a therapeutically effective amount for treating AIDS.

* * * * *